United States Patent [19]

Thomas et al.

[11] 4,392,993
[45] Jul. 12, 1983

[54] ALICYCLIC UNSATURATED COMPOUNDS, THEIR PREPARATION AND USE OF SAME AS PERFUME INGREDIENTS

[75] Inventors: Alan F. Thomas, Borex/VD; Ferdinand Näf, Geneva, both of Switzerland

[73] Assignee: Firmenich, SA, Switzerland

[21] Appl. No.: 286,269

[22] Filed: Jul. 23, 1981

[30] Foreign Application Priority Data

Aug. 22, 1980 [CH] Switzerland .......................... 6342/80

[51] Int. Cl.$^3$ ............................ A61K 7/46; C11B 9/00
[52] U.S. Cl. ................................ 252/522 R; 568/377; 568/826; 252/174.11
[58] Field of Search .................... 568/377; 252/522 R, 252/174.11

[56] References Cited

U.S. PATENT DOCUMENTS

| | | | |
|---|---|---|---|
| 3,734,967 | 5/1973 | Hoffmann et al. | 568/377 |
| 4,006,108 | 2/1977 | Ochsner et al. | 252/522 R |
| 4,136,066 | 1/1979 | DeHaan et al. | 252/522 R |
| 4,179,448 | 12/1979 | Schulte-Elte | 568/377 |
| 4,260,527 | 4/1981 | Trenkle et al. | 252/522 R |

*Primary Examiner*—John F. Niebling
*Attorney, Agent, or Firm*—Scully, Scott, Murphy & Presser

[57] ABSTRACT

New alicyclic unsaturated compounds useful as perfume ingredients and perfume compositions containing same. The new compounds have formula

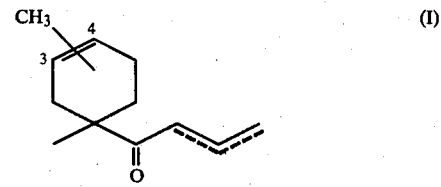

possessing a methyl group attached to the carbon atom at position 3 or 4 of the ring and one double bond in one of the positions of the carbonyl side chain as indicated by the dotted line.

Process for their preparation from new hydroxy compounds of formula

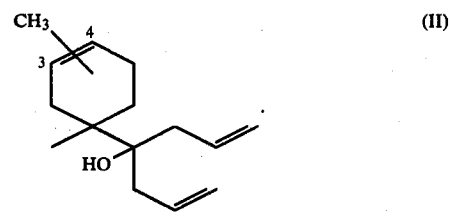

7 Claims, No Drawings

ALICYCLIC UNSATURATED COMPOUNDS, THEIR PREPARATION AND USE OF SAME AS PERFUME INGREDIENTS

SUMMARY OF THE INVENTION

The invention relates to new alicyclic unsaturated compounds of formula

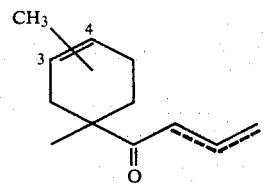

possessing a methyl group attached to the carbon atom at position 3 or 4 of the ring and one double bond in one of the positions of the carbonyl side chain as indicated by the dotted line.

The invention also relates to a method for improving, enhancing or modifying the odour properties of perfumes or perfumed articles, which comprises the step of adding thereto a small but olfactively effective amount of a compound of formula (I).

The invention moreover relates to a perfume composition which comprises as one of its odoriferous ingredients a compound of formula (I).

The invention further relates to a process for preparing a compound of formula (I), which comprises pyrolyzing at a temperature comprised between about 200° and 250° C. a compound of formula

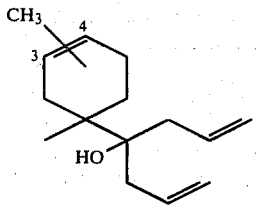

possessing a methyl group attached to the carbon atom at position 3 or 4 of the ring.

The invention finally relates to the compounds of formula (II), which are also new chemical entities.

BACKGROUND OF THE INVENTION

Several alicyclic compounds, namely ketone derivatives, are among the variety of synthetic compounds presently at the perfumers' disposal.

In order to further enlarge the choice of available ingredients and thus enable the creation of novel and original odour notes, we have synthesized a series of new compounds. These are alicyclic unsaturated ketones as defined in formula (I) hereinabove, more particularly 1-(1,3-dimethyl-cyclohex-3-en-1-yl)-but-2-en-1-one, 1-(1,4-dimethyl-cyclohex-3-en-1-yl)-but-2-en-1-one, 1-(1,3-dimethyl-cyclohex-3-en-1-yl)-but-3-en-1-one and 1-(1,4-dimethyl-cyclohex-3en-1-yl)-but-3-en-1-one.

We have unexpectedly discovered that the above compounds possess useful odour properties and consequently can be advantageously used in the art of perfumery.

PREFERRED EMBODIMENTS OF THE INVENTION

The alicyclic unsaturated ketones of the instant invention can be used for developing various odour notes of green, flowery, fruity and aromatic type.

Their dominant fruity character can be defined as reminiscent of that of certain ripe exotic fruits, melon for example. The flowery note is reminiscent of that of fresh camomile whereas the aromatic note can be defined as natural, herbaceous and somehow thuyone-like.

Due to their original odour, compounds (I) can be advantageously used for the manufacture of perfume compositions or perfume bases of various types. They can also be used for perfuming products such as soaps, detergent powders, shampoos, waxes, deodorizing products or cosmetic preparations to which they impart a pleasant character.

The proportions at which the said compounds can achieve interesting perfuming effects can vary within wide limits depending on the nature of the perfumed article or on the specific effect it is desired to achieve. These proportions can preferably be of the order of 1 to 10, or even 20% by weight, based on the total weight of the composition in which they are incorporated. These values, however, should not be interpreted restrictively and it should be understood by those skilled in the art that concentrations lower or higher than those indicated above may also be used in practice.

The compounds of the instant invention can be prepared by subjecting the diallyl alcohols of formula (II) to pyrolysis. Said pyrolysis is carried out preferably in an autoclave, in the presence of an inert organic solvent such as a cycloaliphatic hydrocarbon, cyclohexane for example. The reaction temperature is generally comprised between about 200° and 250° C., preferably between about 230° and 240° C. These values must not be interpreted restrictively; higher temperatures can in fact also be successfully applied to carry out the said pryolysis. We noted however that at temperatures of about 300° C. or more, one could not suppress the formation of undesired by-products having a negative odour effect on the thus obtained material.

We also noted, finally, that good yields of end products could be obtained by adding small quantities of anhydrous sodium carbonate to the reaction mixture.

The instant invention will be illustrated in a more detailed manner by the following examples wherein the abbreviations possess the sense common in the art (temperatures in degrees centigrade).

EXAMPLE 1

Perfumed Detergent Powder

A commercial detergent powder was intimately mixed with a proportion of 0.1% (by weight) of 1-(1,4-dimethyl-cyclohex-3-en-1-yl)-but-2-en-1-one. The powder thus perfumed possessed a pleasant and natural odour character.

By replacing in the above example the cited perfume ingredient by an identical amount of its isomer, 1-(1,3-dimethyl-cyclohex-3-en-1-yl)-but-2-en-1-one, or by any isomeric mixture of the two of them, analogous odour effects were achieved.

EXAMPLE 2

Perfumed Shampoo

A commercial shampoo base was perfumed with a proportion of 0.3% (by weight) of 1-(1,3-dimethyl-cyclohex-3-en-1-yl)-but-2-en-1-one. The thus perfumed shampoo possessed an original odour note of "medicinal" type which increased the health-care character of the product.

By replacing in the above example the cited perfume ingredient by an identical amount of its isomer, 1-(1,4-dimethyl-cyclohex-3-en-1-yl)-but-2-en-1-one, or by any isomeric mixture of the two of them, analogous odour effects were achieved.

EXAMPLE 3

Perfume Base Composition for Shampoos

| Ingredients | Parts by weight |
| --- | --- |
| Synthetic linalool | 200 |
| α-Amylcinnamic aldehyde | 150 |
| Phenoxyethyl butyrate | 100 |
| Benzyl salicylate | 80 |
| Benzyl benzoate | 60 |
| Limonene | 50 |
| Citronellyl isobutyrate | 40 |
| HEDIONE ®[1] | 40 |
| GLYCOMEL[1][4] 10%* | 40 |
| Galbanum resinoid | 40 |
| α-Damascone[1][2] 10%* | 40 |
| Phenylethyl acetate | 30 |
| TONALIDE ®[3] | 20 |
| Total | 900 |

*in dipropylene-glycol
[1]origin: FIRMENICH SA, Geneva, Switzerland
[2]DORINONE ®
[3]see S. Arctander, Perfume and Flavor Chemicals, Section 41 (1969). Montclair N.J. (USA)
[4]Methyl 3-methyl-3-(norbornen-5-yl)-glycidate (see U.S. Pat. No. 4,252,728).

By adding 100 g of 1-(1,3-dimethyl-cyclohex-3-en-1-yl)-but-2-en-1-one to 900 g of the above base composition, there was obtained a new perfume composition the odour character of which was richer and more fruity than that of the base and which became rounder and more lifting after a certain time.

By replacing in the above example the cited perfume ingredient by an identical amount of 1-(1,4-dimethyl-cyclohex-3-en-1-yl)-but-2-en-1-one or by any isomeric mixture of the two of them, analogous odour effects were achieved.

EXAMPLE 4

Preparation of Compounds of Formula (I)

(a) To 7.5 g of magnesium turnings in 30 ml of anhydrous tetrahydrofuran (THF), there were added under nitrogen atmosphere 2.4 g of allyl bromide followed by a mixture of 21.6 g of allyl bromide and 25 g of methyl dimethylcyclohexenyl-carboxylate in 350 ml of anhydrous THF. The addition was effected at 20°-25° over a period of 2 hours, whereupon the reaction mixture was stirred during 2 hours at room temperature. After having been poured into an ice-cooled saturated aqueous solution of ammonium chloride, the reaction mixture was extracted with ether (3×100 ml), the combined organic extracts washed with water until neutrality (4×100 ml), dried and evaporated to afford 30 g of a fraction constituted by a mixture of diallyl alcohols which can be represented by the following formula

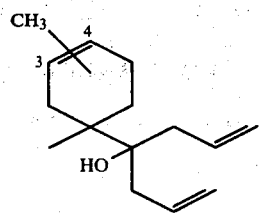

The obtained mixture was further purified by distillation to afford 26 g of a product having b.p. 65°-78°/10 Torr.

(b) 150 g of the purified mixture as obtained according to letter (a) in 150 ml of a cyclohexane were heated in a 500 ml autoclave at 230°-240°, in the presence of 1 g of anhydrous sodium carbonate (reaction time: 7 hours). After cooling and rapid distillation of the reaction mixture, the following fractions were isolated:

(1) 50.1 g having b.p. 50°-56°/0.1 Torr
(2) 36.0 g having b.p. 56°-64°/0.04 Torr
(3) 13.1 g having b.p. 64°-71°/0.04 Torr.

Fraction no. 3 contained 24% of a mixture of the desired compounds and 76% of starting mixture of diallyl alcohols.

A further purification of the above fractions by preparative vapour phase chromatography afforded 63 g of a mixture containing about 65% (by weight) of 1-(1,4-dimethyl-cyclohex-3-en-1-yl)-but-2-en-1-one and 35% (by weight) of the corresponding 1,3-dimethyl isomer, followed by 11.6 g of a second mixture containing 1-(1,3-dimethyl-cyclohex-3-en-1-yl)-but-3-en-1-one and its corresponding 1,4-dimethyl isomer.

Both 1(1,4-dimethyl-cyclohex-3-en-1-yl)-but-2-en-1-one and 1-(1,3-dimethyl-cyclohex-3-en-1-yl)-but-2-en-1-one were obtained in the pure state by making use of corresponding pure diallyl alcohol, viz. 1-(1,4-dimethyl-cyclohex-3-en-1-yl)-1-allyl-1-hydroxy-but-3-ene and 1-(1,3-dimethyl-cyclohex-3-en-1-yl)-1-allyl-1-hydroxy-but-3-ene, respectively.

Said alcohols were previously separated by means of column chromatography on silicagel (Jobin-Yvon apparatus).

The spectral data of the obtained compounds are given hereinbelow:

1-(1,3-dimethyl-cyclohex-3-en-1-yl)-1-allyl-1-hydroxy-but-3-ene

NMR: 0.92; 1.6 δ ppm;
MS: m/e: 69(100), 41(80); 109(61), 95(41), 43(40), 179(29), 161(16).

1-(1,4-dimethyl-cyclohex-3-en-1-yl)-1-allyl-1-hydroxy-but-3-ene

NMR: 0.92, 1.59 δ ppm;
MS: m/e: 69(100), 41(77), 109(67), 43(96), 95(30), 161(29), 179(27).

1-(1,4-dimethyl-cyclohex-3-en-1-yl)-but-2-en-1-one

NMR: 1.13; 1.63; 1.88 (d, J=6.5 Hz); 2.25-2.65 (1H, broad d); 5.34 (1H, broad s); 6.5 (1H, d, J=15 Hz); 6.96 (qxd, J=6.5 and 15 Hz) δ ppm;
MS: M+=178(34); m/e: 109(100), 69(80), 67(59), 163(53), 41(50), 93(26).

1-(1,3-dimethyl-cyclohex-3-en-1-yl)-but-2-en-1-one

NMR: similar to that of the 1,3-dimethyl isomer

MS: M+=178(4); m/e: 109(100), 69(47), 67(27), 41(24), 108(15), 93(13), 163(9).

1-(1,4-dimethyl-cyclohex-3-en-1-yl)-but-3-en-1-one

NMR: 1.12; 1.64 δ ppm;

MS: M+=178(19); m/e: 109(100), 69(46), 67(45), 41(34), 163(24), 18(17).

1-(1,3-dimethyl-cyclohex-3-en-1-yl)-but-3-en-1-one

NMR: 1.13, 1.68, 4.9-5.4(2H, m); 6.0-6.5(2H, m) δ ppm;

MS: M+=178(1); m/e: 109(100), 69(33), 67(26), 41(20), 163(3).

What we claim is:

1. A compound of formula

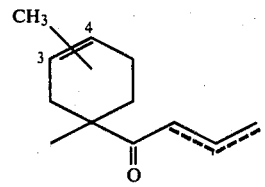

(I)

possessing a methyl group attached to the carbon atom at position 3 or 4 of the ring and one double bond in one of the positions of the carbonyl side chain as indicated by the dotted line.

2. 1-(1,3-Dimethyl-cyclohex-3-en-1-yl)-but-2-en-1-one.

3. 1-(1,4-Dimethyl-cyclohex-3-en-1-yl)-but-2-en-1-one.

4. 1-(1,3-Dimethyl-cyclohex-3-en-1-yl)-but-3-en-1-one.

5. 1-(1,4-Dimethyl-cyclohex-3-en-1-yl)-but-3-en-1-one.

6. Method for improving, enhancing or modifying the odour properties of perfumes or perfumed articles, which comprises the step of adding thereto a small but olfactively effective amount of at least one of the compounds of claims 1 to 5.

7. A perfume composition which comprises as effective ingredient at least one of the compounds of claims 1 to 5.

* * * * *